United States Patent [19]

Maurer et al.

[11] 4,055,655

[45] Oct. 25, 1977

[54] COMPLEXES OF HEAVY METAL IONS AND POLYFUNCTIONAL ORGANIC LIGANDS USED AS ANTIMICROBIAL AGENTS

[75] Inventors: Gerald L. Maurer, Fairfield; Sudhir K. Shringapurey, Cincinnati; both of Ohio

[73] Assignee: National Research Laboratories, Cincinnati, Ohio

[21] Appl. No.: 597,756

[22] Filed: July 21, 1975

[51] Int. Cl.$^2$ ............................................. A01N 9/00
[52] U.S. Cl. ................................. 424/294; 424/289; 424/290; 424/291; 424/292; 424/295; 424/296; 424/287
[58] Field of Search ............... 424/294, 289, 290, 291, 424/292, 295, 296, 287

[56] References Cited

U.S. PATENT DOCUMENTS

| | | | |
|---|---|---|---|
| 3,076,834 | 2/1963 | Norton | 424/294 X |
| 3,300,498 | 1/1967 | Gershon et al. | 424/245 X |
| 3,799,945 | 3/1974 | D'Amico | 424/245 X |

OTHER PUBLICATIONS

Bobtelsky et al. JACS. 67, pp. 1824–1831 (1945).
Chemical Abstracts 75:31794q (1971).
Chemical Abstracts 63:7876h (1965).
Chemical Abstracts 57:371d (1962).

*Primary Examiner*—Leonard Schenkman
*Attorney, Agent, or Firm*—Wood, Herron & Evans

[57] ABSTRACT

Antimicrobial agents are disclosed containing as the active ingredient a metal complex of a metal ion and a polyfunctional organic ligand. The antimicrobial metal complexes are characterized by a very unexpected aqueous proton induced dissociation property which causes the controlled release of toxic metal ion at a pH compatible with microorganism growth. This dissociation property is represented by a sigmoidally shaped curve, i.e., one curved in two different directions like the letter "S," on a cartesian coordinate plot of the negative logarithm (log) of metal ion concentration versus the negative logarithm (log) of hydrogen ion concentration (or otherwise known as a pM-pH diagram). Antimicrobial metal complexes are also disclosed which are extremely effective in the controlled release of metal ion from the complex in about the normal range of physiological pH, i.e., about $10^{-4}$ to $10^{-9}$ moles of hydrogen ion per liter.

14 Claims, 1 Drawing Figure

Figure 1:
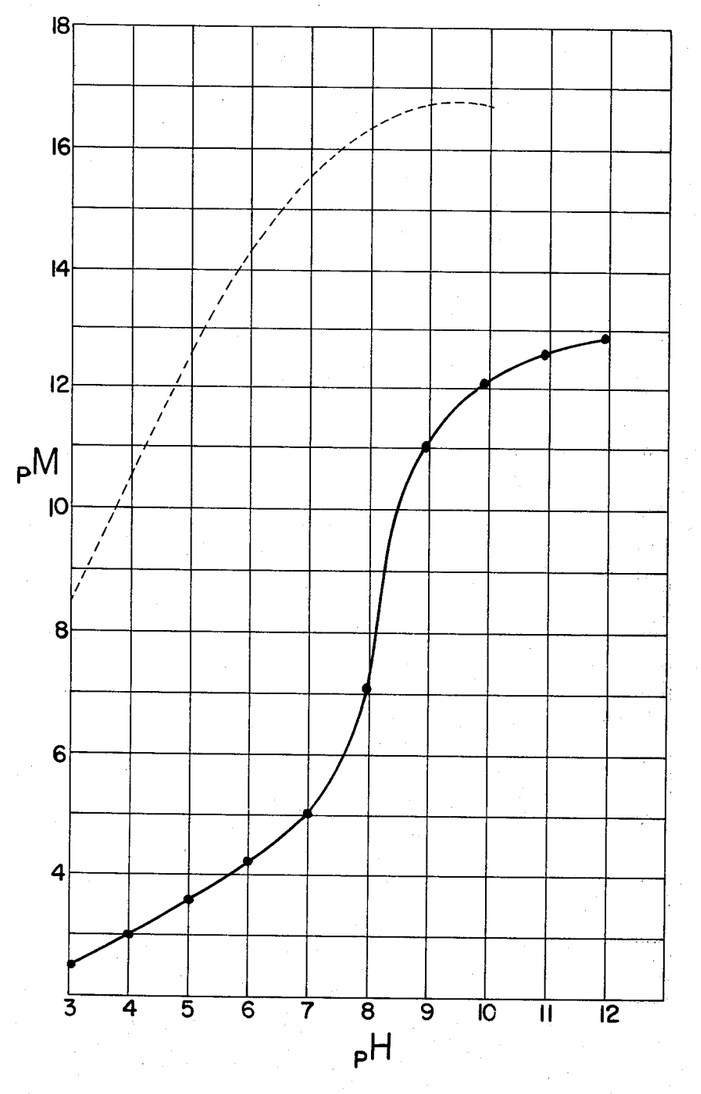

COMPLEXES OF HEAVY METAL IONS AND POLYFUNCTIONAL ORGANIC LIGANDS USED AS ANTIMICROBIAL AGENTS

BACKGROUND OF THE INVENTION

Many kinds of substances have a deleterious effect on microorganisms. Antimicrobial substances have two kinds of activity, the one bacterial, germicidal or virucidal, concerned with the killing of microorganisms; and the other bacteriostatic or growth-inhibiting. Antimicrobial activity is a property of both inorganic and organic substances, and the exploitation of such activity is a matter of considerable practical importance in the development of antiseptics, sanitizers, germicides, bactericides, sporicides, virucides and disinfectants.

A number of inorganic substances have antimicrobial activity because of the toxicity to microoganisms of the ions into which they dissociate; or because of their activity as oxidizing agents which brings about some degree of oxidation of cell substance. Among the inorganic substances which act as antimicrobial agents are salts. The degrees to which salts are effective as toxic agents are mainly dependent upon the degree of dissociation of the salt, the nature of the anion, and the valence and molecular weight of the metallic ion. In general, the bivalent cations are more toxic than the monovalent cations, and the salts of the heavier metals are more toxic than those of the lighter metals. The antimicrobial activity of the heavy metal salts is attributed to the affinity of the cations for protein material; when the constituent protein of the bacterial cell is precipitated as an insoluble proteinate, the cell dies. Other factors may also be involved, however.

The processes of effecting bacterial growth-inhibition or death are subject to a variety of influences. The most important of these influences is the concentration of the reacting substances, i.e., concentration of the biocidal substance and the numbers of bacteria present. The effective concentration of a biocidal substance is, in turn, dependent upon primarily two other factors: first, the presence of moisture, which makes possible ionization of the substance to form the biocidal agent and acts as a suspending medium in which there may be intimate contact between the biocidal agent and the microorganism. Second, presence of extraneous organic and/or other matter which will react with the agent prior to contact with an organism thereby rendering the agent ineffective.

Metal salts or metal complexes have been used as antimicrobial agents. Representative of prior art patents directed to the use of metal salts or metal chelates of inorganic or organic compounds as microbiocidal agents include: U.S. Pat. Nos. 871,392; 991,261; 1,679,919; 1,785,472; 2,208,253; 2,269,891; 2,456,727; 2,494,941; 2,878,155; 2,900,303; 2,901,393; 2,938,828; 3,076,834; 3,099,521; 3,206,398; 3,240,701; 3,262,846; 3,266,913; 3,681,492 and 3,782,471.

It has been established in antimicrobial activities that salts of heavy metals are rapidly precipitated by extraneous organic or other material and, therefore, while such salts may have an initial cell kill at an initial effective concentration, the effective concentration is rather quickly reduced by combination of the metal with such extraneous matter, thereby depleting the amount of toxic metal available for biocidal activity. Therefore, while inorganic salts offer in certain instances the property of aqueous solubility and, therefore, dissociation for availability as toxic metal agents, they may be rendered rather quickly ineffective such that prolonged or controlled destruction or inhibition of bacterial action is unavailable. On the other hand, metal salts or complexes of organic moieties such as organic acids or the like possess a degree of dissociation which is normally not as great in comparison to, for example, highly soluble inorganic salts. Therefore, whereas the metal organic salts or metal complexes may have a greater stability or kinetic inertness with respect to extraneous organic matter present in the environment of living cells, there is also generally a loss of toxic effect by reason of their higher stability.

Superimposed on this brief background discussion of antimicrobial activity is the relation of bacterial growth to the acidity or alkalinity of the media conducive to such growth. Concentrations of hydrogen ions compatible with growth are very low, generally, on the order of about $10^{-4}$ to $10^{-9}$ moles of hydrogen ions per liter. Almost all bacteria will grow at about pH 7.0 ($1 \times 10^{-7}$ moles hydrogen ion per liter) but thrive best at optimum pH's which vary from species to species. The minimum and maximum limits between which viability is possible likewise vary widely with species. The activity, therefore, of an antimicrobial agent in the pH range of microbial viability is a very important consideration in that the activity determines biocidal efficacy.

In substance, heretofore in the prior art there appear to have been two extremes made available by antimicrobial metallic compositions. On the one hand, known metal compounds have a high degree of dissociation such that toxic metal ions are quickly and copiously made available by virtue of rapid dissociation with formation of ionized species. These species react so as to saturate all available ligands; and thereby are rendered inactivated as to cidal potential in a very narrow time frame, obviating residual killing power, thus rendering them relatively ineffective as biocidal agents over prolonged periods of time. Other known metal compounds are relatively stable and provide minimal amounts of ionized species over the normal physiological pH range, providing, therefore, minimal growth inhibitory or toxic potential, due to the very minimal degree of dissociation inherent in them.

SUMMARY OF THE INVENTION

This invention is predicated in part upon the discovery of an antimicrobial metal complex having a proton induced dissociation property which renders it particularly unique and effective in concentrations of hydrogen ions compatible with microorganism viability. The active ingredient for antimicrobial activity according to this invention is a metal complex of a metal ion and a polyfunctional organic ligand. These metal complexes have also been found to have a very unexpected dissociation property in about the normal range of physiological pH. The dissociation property is represented by a sigmoidally shaped curve, i.e., one curved in two different directions, like the letter S, on a cartesian coordinate plot of the negative log of metal ion concentration versus the negative log of hydrogen ion concentration (or otherwise known as a pM-pH diagram). This unique dissociation property of the antimicrobial metal complexes thereby renders them extremely effective in the controlled release of toxic metal ion from the complex at a pH compatible with growth of bacteria. The antimicrobial agents are very effective as microbiocides and bacteriostats for microorganisms including bacteria, fungi and viruses.

In another unique aspect of this invention, antimicrobial metal complexes are provided which are very stable at high alkaline pH's on the order of about 9 to about 12 and, therefore, such complexes are very advantageously employed in alkaline media providing controlled release, upon demand, of their antimicrobial activities. As will fully be appreciated in the detailed description of this invention, and the examples which follow, the antimicrobial agents of this invention are active against broad spectrums of microorganisms.

Furthermore, this invention fulfills a need in another of its features in a manner heretofore unknown in antimicrobial agents by employment of a metal complex of a polyfunctional organic ligand which releases toxic metal ion in large amounts in the normal range of physiological pH, i.e., about 4 to about 9. In particular, antimicrobial agents of this invention release large amounts of toxic metal ion from their coordinate structures at a pH between about 7 and 9, and are effectively unstable at about pH 7 where almost all microorganisms are viable. These antimicrobial agents are very stable and relatively inert to organic moieties, unlike multivalent soluble salts of the prior art which usually are caused to precipitate. Such agents are extremely stable even at high alkaline pH's. Yet, upon demand, by reason of their unique dissociation property as demonstrated by sigmoidally shaped behavior on a pM-pH diagram, these agents offer controlled release of metal ions at a pH where nearly all bacteria are believed to grow. Such a structural entity which offers dissociation upon demand at the pH most amenable to the viability of bacteria, and is readily accepted into the internal cellular structure of bacteria, is a unique discovery. The metal complexes of this invention by reason of their organic ligand nature render them particularly stable against extraneous organic moieties present in bacterial cells or in a surrounding environment.

The antimicrobial complexes of this invention are therefore to be differentiated from other metal complexes wherein metal cations have been complexed with organic ligands represented by ethylenediaminetetraacetic acid (EDTA), diethylenetriamine-pentaacetic acid (DTPA), other amino acids, or the like which have relatively high stability or chemical inertness and which do not offer a controlled release of toxic metal ion or dissociation property represented by a sigmoidal pM-pH diagram. Rather, known metal complexes by reason of their stability and chemical inertness will tend to dissociate to a lesser extent in rather linear fashion over the normal physiological pH range.

Furthermore, this invention provides an antimicrobial metal complex which is capable of aqueous solubility in high concentration by reason of its ionic character and yet remains in a stable form. This property of solubility in water of in neutral, acid or alkaline media enables the production of concentrates capable of producing upon demand toxic metal ion in a physiological pH environment. Such a solubility property is to be distinguished from the rather insoluble metal compounds of the prior art which employ metal cation-anionic components and which are virtually insoluble in aqueous media; or those metal complexes which, even though they are soluble, bind the metal ion in such a complex state that it is only slightly dissociated and, therefore, scarcely available for toxic action.

In a presently preferred form, the antimicrobial agent of this invention comprises a monomental complex of a multivalent metal and a polyfunctional organic ligand in a ratio of 1:1 of the metal to the ligand, the complex having a dissociation property represented by a sigmoidally shaped plot on a pM-pH diagram. A specific example of the metal complex is dialkali metal monocopper(II) citrate represented by disodium-, dipotassium- or dillthium- monocopper(II) citrate. These dialkali monocopper(II) citrates have a dissociation property represented by a sigmoidal plot wherein the curve of two directions meets at a point within the pH range of about 7 to about 9. It has been established that these monocopper(II) complexes in basic media, on the order of about 9 to about 12, are very stable, i.e., having an effective stability constant, $K_{eff}$, on the order of about $10^{12}$ to about $10^{13}$. However, $K_{eff}$ of these monocopper(II) citrate complexes at a pH of about 7-8 is on the order of about $10^5$ to about $10^8$. Therefore, at or about a pH around 7-8, or nearly the physiological pH of about 7.4, the effective stability constant of the monocopper(II) citrate complex is considerably lower (a thousand to several hundreds of thousands times lower) and a significant free $Cu^{++}$ concentration is available for toxic activity. For example, about 10% of the copper in the complex is in the ionized state at or about pH 7 while approximately 0.1% of the copper is ionized at or about pH 9. This would not be true for an EDTA or polyamine complex of a multivalent metal such as copper, since its stability constant ($10^{14}$ to $10^{16}$) will vary only slightly in the normal pH of microbe viability. Such EDTA complexes do exhibit a pH effect on the stability constant, but it is represented by a smooth, monotonic curve reaching a limiting effect by proton induced dissocation at pH values from about 7 to about 9, yielding only from about 0.001% ionized species at or about pH 7 to as little as 0.00001% ionized species at or about pH 9. It is to be understood that the antimicrobial complexes will operate over a pH range of about 3 to about 12. Above about pH 12, the complexes tend to be destroyed by the alkaline media, precipitating from the media as hydrous metal oxides. Below about pH 6, i.e., about 3 to about 6, the instability of the metal complex results in a high concentration of the free $Cu^{++}$ in solution which will perform toxic functions. In the mid range of about 7 to about 9, the controlled release is most effective. Thus, this invention provides controlled release of toxic metal ion between about 10% to about 0.1% of a complexed metal in the pH range of about 7 to 9.

Another important feature of the antimicrobial complexes of this invention is believed to be operative which enables them to function as very effective bactericides. This is exemplified where bacteria are growing in a media having a pH, for example, of about 9 to about 11 and where a dialkali monocopper(II) citrate complex is introduced. As developed above, the alkaline pH environment renders the monocopper(II) citrate complex very stable. It is hypothesized that the free copper ion would not, by reason of its immediate attachment to the cell surface, be expected to transport across the cell membrane at all or, at best, not as readily as the complex form. On the other hand, the complex is readily transported across the cell membrane possibly because of (1) its organic nature which could serve as a metabolic substrate upon which bacterial growth or proliferation depends, or (2) the low charge dianionic density of the complex which enhances permeability through the bac- terial cell wall. After transport across the cell membrane, it is expected that the complex would be subjected to a pH environment on the order of about 7. Therefore, after transportation, the particular complex is very unstable and labile, therefore the copper ion is abundantly and rapidly released for denaturization of cell protein or other metabolic interference with the intracellular biochemical reactions so as to cause cell death. In contrast, where other known complexes may be transported under such circumstances, such known complexes are rather stable and kinetically inert and will not be effective because copper is too tightly bound even at the intracellular pH of approximately 7 for it to be exceedingly toxic.

In accordance with this description and the presently preferred embodiment, it will become apparent that other antimicrobial metal complexes of polyfunctional organic ligands respond to the model of this invention where they exhibit the dissociation property characterized by a sigmoidally shaped curve on a standard pM-pH diagram. For example, based upon the monometal-polyfunctional organic ligand complex of this invention as a microbiocidal agent, other metal ions of a monovalent or polyvalent nature, specifically monovalent, bivalent and polyvalent cations including zinc, nickel, chromium, bismuth, mercury, silver, cobalt, and other similar metallic or heavy metal cations may be employed. The complexes of heavier metals are considered more toxic than those of the lighter metals. Other polyfunctional organic ligands may be substituted for the citric acid specifically exemplified by the preferred embodiment of this invention. Included among other polyfunctional ligands are the broader class of alpha or beta hydroxy polycarboxylic acids into which class the citric acid falls. Also, other functionally substituted acids such as alpha or beta amino, sulfhydro, phosphinol, etc., can be substituted in the molecular model of the metal complexes of this invention and similar results can be achieved. In general, from a metal complex formula standpoint, the monomental complex of copper and citric acid corresponds to a complex formula exhibited by either of the following structural form (A) or (B).

The (A) form is believed to be the more preferred form by applying free energy considerations. A single proton introduced into the complex structure represented by either form (A) or (B) prevents the formation of stable 5- or 6- member coordinate rings. With the Introduction of a proton, only 7- member rings may be formed by the coordination of the acetate electron donors and such 7- member ring structures are unstable. Therefore, the complex molecule dissociates and presents the metal ion for its toxic effects. In comparison, metal complexes of EDTA or other polyamines require four or more protons, and hence greater acidity, to dissociate the complex; this accounts for the small pH effect exhibited by such complexes in a pM-pH diagram.

The (A) and (B) structural forms may be more generally represented by the following models:

In the above models, the solid line segments represent a chemical bond between elements in the skeletal structure of the molecule; X, Y and Z represent electron pair donors; (R) represents any elemental or molecular species or group; M represents a metal and wherein the proton affinity of X is greater than that of Z, Y or R. It will therefore be appreciated that other Lewis base proton pairs, and other metal ions, may be substituted into these structural models for oxygen, divalent copper, or, for that matter, the carbon atoms to provide a molecular model which will similarly dissociate upon the introduction of one proton or similarly behaving species as exhibited by the sigmoidal behavior on a pM-pH diagram. The molecular models are thus alternative expressions for the antimicrobial agents of this invention.

The invention and its various embodiments and advantages will be further understood with reference to the following examples, detailed descriptions and the drawing which illustrate the preparation and activity of the antimicrobial complexes.

PREPARATION OF ANTIMICROBIAL COMPLEXES

A. Dilithium monocopper(II) citrate 10 millimoles of lithium citrate were dissolved in 10 milliliters of water. To this solution, 10 millimoles of cupric chloride ($CuCl_2 \cdot 2H_2O$) were added gradually with stirring. A deep blue solution was formed. This was neutralized to a pH of about 7 with 10 millimoles of lithium hydroxide ($LiOH \cdot H_2O$). This solution, when evaporated to dryness, gave a deep blue, semicrystalline solid. This solid was ground to a fine powder and the lithium chloride was extracted with 50 milliliters of dry methanol, five times, at 35° C. The blue solid which remained behind was evacuated to remove methanol and desiccated. An attempt was made to crystallize the salt from water-organic solvent systems, but apparently due to the extremely hygroscopic nature of the salt and the high negative charge on the ionized molecule, the solid obtained was microcrystalline to amorphous. The following formula is proposed for the 1:1 complex of copper and citrate based on elucidation of the structure and analyses described hereinafter.

$Li_2CuC_6H_4O_7 \cdot XH_2O$

Depending upon the degree of hydration, the following formula weights (F.W.) and corresponding percentages of copper content are proposed:

$Li_2CuC_6H_4O_7 \cdot XH_2O$

| | | |
|---|---|---|
| F.W.: | 265.51 for X=0, | % Cu = 23.93 |
| F.W.: | 283.53 for X=1, | % Cu = 22.41 |
| F.W.: | 301.54 for X=2, | % Cu = 21.07 |
| F.W.: | 319.56 for X=3, | % Cu = 19.88 |

The observed copper content of variously dried samples of the solid complex ranged from 20% to 23%. The compound (1:1 solid complex) was extremely soluble in water. A solution as strong as two molar could be made quite easily. Up to a pH of 11.5, there was no effect on the solubility of the compound in water. Beyond this pH, the complex decomposed to a greenish-brown precipitate, probably hydrous copper oxides. The 1:1 solid complex may be used as an antimicrobial agent with or without the removal of lithium chloride formed during its preparation.

B. Disodium monocopper(II) citrate

1. Equimolar solutions of copper chloride and sodium citrate were added to water as in A above to obtain a deep blue solution having a pH of abour 5. A 50 ml. aliquot of this solution was placed in a separatory funnel. An equal volume of anhydrous acetone was added and the funnel was shaken so as to effect mixing. Upon standing, a two-phase system existed. A blue liquid phase rested on the bottom of the funnel in a reduced volume of approximately 25 ml., while the top layer (approximately 75 ml.) was slightly hazy and colorless, having been crystal clear prior to the shaking process. The blue liquid (oily, viscous) was removed from the funnel through the stopcock and collected in a second separtory funnel. The hazy supernatant was placed in a breaker and evaporated to dryness over a steam bath. An approximately 25 ml. aliquot of anhydrous acetone was added to the second separatory funnel, causing almost instantaneous formation of a plastic-like mass in the bottom of the funnel, as opposed to the oily liquid which had been present there. The supernatant from the plastic mass was placed in a second beaker and labeled supernatant 2. The addition of distilled water to the plastic-like mass resulted in in the immediate re-solution of the material. The total volume of the redissolved substance was adjusted to 25 ml., resulting in the formation, once again, of a viscous, oily liquid. Following evaporation to dryness of supernatant 1, microscopic examination of the dry residue revealed the presence of definite, copious amounts of sodium chloride crystals. Evaporation of supernatant 2 yielded a very finely divided powdery residue, containing a small number of distinct sodium chloride cyrstals. Analysis of the twice-extracted blue oily solution for copper content revealed that the solution contained approximately 125 mg. of copper per milliliter, thereby representing a concentrate of the metal complex which had originally contained approximately 65 mg. per milliliter. The large reduction of the amount of sodium chloride in supernatant 2 indicated that the bulk of the contaminating by-product salt had been removed. A portion of the concentrate was permitted to evaporate and definitive crystalline material was noted.

2. The procedures of the preceding paragraph (1) were repeated except that there was a pH adjustment of the initially formed blue solution from about pH 5 to about pH 7 with KOH solution to neutralize the HCl formed. After extraction and evaporation procedures were performed as above, a concentrate of the metal complex was obtained which upon evaporation yielded definite crystalline material.

3. Equimolar aliquots of copper sulfate and sodium citrate as in paragraph (1) were combined followed by pH ajustment of about 7 with NaOH. Procedures of extraction and evaporation of the resulting blue solution as described above yielded an amorphous powder possessing no visually discernible crystalline structure.

The following formula is proposed for the disodium monocopper(II) citrate prepared in paragraphs (1) to (3) above based on the elucidation of the structure and analyses described hereinafter:

$Na_2CuC_6H_4O_7 \cdot XH_2O$

DETERMINATION OF ANTIMICROBIAL COMPLEX DISSOCIATION (STABILITY)

The dissociation and stability of the metal complexes are related properties. Expressed mathematically the stability constant is the logarithm of the reciprocal of dissociation or ionization. The dissociation property of the 1:1 copper citrate complex prepared by the above techniques was determined over a pH range of 3-12 units using a copper(II) ionspecific electrode (Orion Copper(II) Specific Electrode). 50 milliliter samples of coppeer citrate 1:1 solution (0.0068 molar) were adjusted to pH 3, 4, 5, 6, 7, 8, 9, 10, 11 and 12, with the concentration of free copper ion subsequently determined by using the copper ion specific electrode. The following values of free copper ion concentrations at the indicated pH were obtained and the negative logs of the copper ion concentration determined.

TABLE

| pH | Cu++ | pM |
|---|---|---|
| 3 | $3.2 \times 10^{-3}$ | 2.495 |
| 4 | $9.0 \times 10^{-4}$ | 3.046 |
| 5 | $2.5 \times 10^{-4}$ | 3.602 |
| 6 | $5.3 \times 10^{-5}$ | 4.276 |
| 7 | $1.0 \times 10^{-5}$ | 5.000 |
| 8 | $8.0 \times 10^{-8}$ | 7.097 |
| 9 | $8.8 \times 10^{-12}$ | 11.055 |
| 10 | $9.6 \times 10^{-13}$ | 12.018 |
| 11 | $3.3 \times 10^{-13}$ | 12.482 |
| 12 | $1.34 \times 10^{-13}$ | 12.873 |

From this data, a pM-pH curve was constructed to indicate the relationship between free Cu++ ion concentration and pH as illustrated in the drawing. The drawing is a cartesian coordinate plot (solid black line) of the negative log of the metal ion concentration (pM) versus the negative log of the hydrogen ion concentration (pH) at points listed in the above TABLE. This plot is a sigmoidally shaped curve representative of the proton induced dissociation property of the metal complex. At the pH range of about 9-12, the complex is very stable and the free Cu++ is low. At a pH of about 7, the complex is relatively unstable and dissociation into free Cu++ is significant, enabling toxic function. In the range of between about 7 to about 9 the Cu++ from the complex occurs. This unexpected dissociation versus pH behavior renders the complexes extremely effective as antimicrobial agents.

In comparison, a Cu EDTA complex curve is represented by the broken line in the drawing as reported by A. Ringbom, "Complexation in Analytical Chemistry", J. Wiley & Sons, N.Y., 1963, p. 360. As illustrated, the pH effect on Cu EDTA complex is represented by a smooth, monotonic curve reaching a limiting effect by proton induced dissociation at about pH 7-9, thereby yielding, for example, only from about 0.001%–0.00001% ionized species.

Complexes of the ratio one metal:one citrate may have been suggested to exist in dilute solutions in the publication of M. Bobtelsky and J. Jordan, *J. Amer. Chem. Soc.*, Vol. 67 (1945), p. 1824. However, no one has reported the remarkable antimicrobial activity of these derivatives as we have discovered. Further, we have prepared solid metal complexes of the dialkali monocopper(II) citrates and such solid forms are surprisingly unexpected. We have also been able to make high solution concentrations of such metal complexes. The nature of these complexes has definitely been established by using analytical criteria, namely: (1) the mole ratio method introduced by Yoe and Jones (Yoe, J. H. & Jones, A. L. : *Ind. Eng. Chem. Anal.* Edition, 16; 111, 1944); (2) the method of continuous variation attributed to Job and modified by Vosburgan and Vosburgh (Vosburgh, W. C. & Cooper, G. R.: *J. Am. Chem. Soc.*, 63; 437, 1941); (3) dependence of complex formation on pH and (4) determination of the apparent stability constant of the complex. Spectrophotometric studies, including visible and ultraviolet spectroscopy, pH determinations, as well as infrared spectroscopic measurements were utilized as an additional means of confirmation of our findings on the formation and molecular composition of the 1:1 copper(II) citrate complex.

The metal complexes of this invention have very unique antimicrobial properties in comarison to prior art compounds. For example, formation of heavy metal salts of carboxylic acids is quite common. However, with the exception of salts of lower molecular weight acids, they are usually insoluble in water. This is demonstrated by the dicupric(II) citrate listed in the literature, $(Cu_2citrate)_2 \cdot 5H_2O$. This compound is formed on heating a solution basic solutionn of sodium citrate with $Cu^{++}$. The dicupric citrate (a ratio of 2 copper atoms to 1 citrate ion) precipitates out of solution. This dicupric citrate has the following properties: (1) Insolubility in water (with an overall net charge of the compound being zero; $2Cu^{++}$ and citrate$^{-4}$); the reaction is:

$$2Cu^{++} + \blacksquare Citrate \overset{\Delta}{\rightleftharpoons} Cu_2citrate \downarrow + H^+$$

and is drawn to completion by the reaction of the product $H^+$ with $OH^-$ in basic media, (2) light green in color in solid form, and (3) elemental analysis substantiating 2Cu to 1 citrate ration. The insolubility of the dicupric citrate has also limited the effectiveness of this compound as a bactericide and whereas it has heretofore been proposed in pharmaceutical applications, it use has been limited.

The 1:1 copper complexes employed here as antimicrobial agents are highly soluble indicating that such complexes are ionic in nature. This is further supported by the observation that the color band of solution of the complex migrated towards the anode (positive electrode) in electrophoresis experiments. Visible and UV spectra exhibit 1:1 compound formation. I.R. spectra also differentiate the complexes here and the prior art dicupric(II) citrate. Thus, it is conclusive that a prepared form of the antimicrobial complex of this invention is a Cu-citrate (1:1)= coordination compound which is structurally and chemically different from the previously reported $Cu_2$citrate (2:1). The overall reaction for the antimicrobial complex formation of the (B) structural form appears to be:

(2) $H^+ + OH^- \underset{(base)}{\rightleftharpoons} H_2O$ $$K_{abs} = \frac{[Cu-Citrate^{-2}][H^+]}{[Cu^{+2}][Citrate^{-3}]}$$

$$K_{eff} = \frac{[Cu-Citrate^{-2}]}{[Cu^{+2}][Citrate^{-3}]}$$

Thus, instead of complexing the $COO^-$ groups only, the alcohol, $-OH$, ionizes and is involved in the coordination. This forms a stable 5-member and probably 6-member ring. Thus, the reaction is drawn to the right (stabilized) by $OH^-$ (base) as the product $H^+$ is them removed as the reaction proceeds. This results in the very high effective stability constant, $K_{eff}$. The $K_{eff}$ for such a reaction is pH dependent but related to the absolute stability constant, $K_{abs}$ by the relationships.

$$K_{eff} = \frac{[CuCitrate^=]}{[Cu^{++}][Citrate^{-3}]}$$

$$K_{abs} = \frac{[CuCitrate^=][H^+]}{[Cu^{++}][Citrate^{-3}]}$$

$$K_{abs} = K_{eff}[H^+]$$

We have found that $K_{abs}$ for the 1:1 complex has a constant value of about $10^{13}$ (a strong complex) over a pH range of about 9-12. The apparent value of $K_{abs}$ drops sharply at pH 7 to 9 and, at pH values less than about 7, there is a further decrease indicating that the complex exists in finite concentrations even at pH 3 to 7.

ANTIMICROBIAL ACTIVITY

The following experiments were performed to illustrate the biocidal efficacy of the disodium monocopper(II) citrate of this invention versus the prior art dicupric(II) citrate. The following materials, apparatus and procedures were employed.

Materials

1. Three representative test organisms were chosen for the test:
   a. *Staphylococcus aureus*, designated "SA", ATCC No. 12600
   b. *Aerobacter aerogenes*, designated "AA", ATCC No. 13048
   c. *Pseudomonas aeruginosa*, designated "PA", ATCC No. 10145

ATCC No. is the American Type Culture Collection No.

2. Trypticase soy broth, Difco, prepared in the specified manner by dissolving in hot water and autoclaving, capable of supporting favorable growth in the test organisms.
3. MacLaglan Turbidity Standards for estimation of bacterial growth in broth.
4. Millipore bacterial filter system for estimation of bacterial viability and quantitation of viable organisms.
5. Disodium monocopper(II) citrate, $Na_2CuC_6H_4O_7 \cdot xH_2O$, molecular weight, 297, solid, prepared as above, designated "MCC".
6. Dicupric(II) citrate, $Cu_2C_6H_4O_7 \cdot 2\frac{1}{2}H_2O$, molecular weight, 360, solid, prepared according to National Formulary specifications, designated "DCC".
7. Coleman Jr. Spectrophotometer for quantitation of turbidity, where "OD" is measure of optical density and "OS" means the instrument went off scale due to turbidity.
8. Standard sterile screw-capped culture tubes.
9. Air bath incubator, 35° C.

Method

Three control tubes containing 5.0 milliliters of broth were prepared for each organism to be tested, a total of nine tubes. Each tube set of three was inoculated with approximately $10^6$ organisms per milliliter from a stock culture. The pH of the culture mediums was about 7. Additionally, two spectrophotometer blanks were prepared. MCC and DCC were added to one tube in each set to effect a copper level of 0.5 milligrams per milliliter. Schematically the protocol was as follows in Chart I:

CHART I

| Tube | Broth | S.A. | P.A. | A.A. | MCC | DCC |
|---|---|---|---|---|---|---|
| SA 1 | 5ml | 0.05ml | — | — | 11.7mg | 0 |
| SA 2 | 5ml | 0.05ml | — | — | 0 | 7.1mg |
| SA 3 | 5ml | 0.05ml | — | — | 0 | 0 |
| PA 1 | 5ml | — | 0.07ml | — | 11.7mg | 0 |
| PA 2 | 5ml | — | 0.07ml | — | 0 | 7.1mg |
| PA 3 | 5ml | — | 0.07ml | — | 0 | 0 |
| AA 1 | 5ml | — | — | 0.09ml | 11.7mg | 0 |
| AA 2 | 5ml | — | — | 0.09ml | 0 | 7.1mg |
| AA 3 | 5ml | — | — | 0.09ml | 0 | 0 |

CHART I-continued

| Tube | Broth | S.A. | P.A. | A.A. | MCC | DCC |
|---|---|---|---|---|---|---|
| Blank 1 | 5ml | 0 | 0 | 0 | 11.7mg | 0 |
| Blank 2 | 5ml | 0 | 0 | 0 | 0 | 7.1mg |

Following immediate quantitation and viability testing all tubes were loosely capped and incubated for 48 hours at 35° C, after which the tests were repeated. Results are indicated on Chart II.

CHART II

RESULTS OF QUANTITATION AND VIAIBILITY TESTS

| | Immediate | | | | After 48 Hours | | | |
|---|---|---|---|---|---|---|---|---|
| Tube | Undiluted OD | ±1 /ml | Culture | Plate Count | Undiluted OD | ±1 /ml | Culture | Plate Count |
| SA 1 | .25 | $9.0 \times 10^5$ | Viable | $3.0 \times 10^5$ | .24 | $\sim 8.0 \times 10^5$ | Sterile | 0 |
| SA 2 | .25 | $9.0 \times 10^5$ | Viable | $8.0 \times 10^5$ | OS | $> 3.0 \times 10^6$ | Viable | $400 \times 10^6$ |
| SA 3 | .25 | $9.0 \times 10^5$ | Viable | $8.0 \times 10^5$ | OS | $> 3.0 \times 10^6$ | Viable | $500 \times 10^6$ |
| PA 1 | .35 | $1.3 \times 10^6$ | Viable | $3.0 \times 10^5$ | .36 | $\sim 1.3 \times 10^6$ | Sterile | 0 |
| PA 2 | .35 | $1.3 \times 10^6$ | Viable | $2.0 \times 10^6$ | OS | $> 3.0 \times 10^6$ | Viable | $60 \times 10^6$ |
| PA 3 | .35 | $1.3 \times 10^6$ | Viable | $1.9 \times 10^6$ | OS | $> 3.0 \times 10^6$ | Viable | $50 \times 10^6$ |
| AA 1 | .30 | $1.1 \times 10^6$ | Sterile | 0 | .30 | $\sim 1.1 \times 10^6$ | Sterile | 0 |
| AA 2 | .30 | $1.1 \times 10^6$ | Viable | $10^6$ | OS | $> 3.0 \times 10^6$ | Viable | $400 \times 10^6$ |
| AA 3 | .30 | $1.1 \times 10^6$ | Viable | $10^6$ | OS | $> 3.0 \times 10^6$ | Viable | $400 \times 10^6$ |
| Blank 1 | 0 | 0 | N/A | N/A | 0 | 0 | N/A | N/A |
| Blank 2 | 0 | 0 | N/A | N/A | 0 | 0 | N/A | N/A |

The above test results indicate clearly that MCC possesses marked biocidal activity in reference to all test organisms. Particularly notable is the decrease in viable organisms in the "immediate" phase about 5 minutes after addition of MCC. It is equally obvious that DCC exhibits little, if any, biocidal activity, although some marginal control of *Staphylococcus aureus* was noted after 48 hours of incubation.

Also, these tests demonstrate that MCC is completely soluble in aqueous solutions and hence was easily dissolved in the broth. On the other hand, DCC is insoluble in aqueous media, and forms a cloudy suspension which completely settles out in a few minutes. Therefore, prior to making OD (optical density) readings, the DCC-containing tubes were permitted to settle until a constant reading was obtained, indicating that measured turbidity was, in fact, due to the bacterial particles. The turbidity test, while fairly accurate quantitatively, gives no indication of actual viability of the organisms. Hence, it was necessary to utilize a bio-assay method for determining viability as well as to confirm actual counts of viable organisms.

In addition to the above, the antimicrobial activity of the dialkali monocopper(II) citrates has been established by their toxic and growth-inhibiting action against the following microbes in mediums of oil emulsions employed as coolants in various machining operations where the pH of the coolant baths and liquids were on the order of about 9 to about 10. Such production coolant compositions are described in U.S. Pat. No. 3,244,630 and "American Society of Tool Engineers — Tool Engineer's Handbook", first edition, 1953, pages 357 et sequal, and such disclosures are incorporated herein by reference.

*Aerobacter aerogenes*
*Aspergillus niger*
*Bacteroides*
*Bacillus subtilis*
*Candida albicans*
*Citrobacter*
*Enterobacter cerratia*
*Enterobacter cloacae*
*Escherichia coli*

*Klebsiella-aerobacter*
*Neisseria catarrhalis*
*Proteus (Providence Group)*
*Proteus micrabilis*
*Proteus morgani*
*Proteus rettgeri*
*Proteus vulgaris*
*Pseudomonas aeruginosa*
*Pseudomonas fluorescens*
*Salmonella species*
*Staphylococcus albus*
*Staphylococcus aureus*
*Staphylococcus epidermidis*
*Streptococcus fecalis*
*Streptococcus viridans*

The above efficacy of antimicrobial activity was established in industrial coolant liquids where the listed microbes were found to proliferate. It is significant that even at these high pH's which are necessary for coolant liquid performances, the dialkali monocopper(II) citrates were remarkably effective. It is to be appreciated, furthermore, for example, that approximately 100 times more free copper would be made available at pH 8.5 than at pH 9.5 with reference to the attached drawing of the dissociation curve. Similarly, as the pH decreases below 8.5, even significantly greater amounts of toxic copper ion are released. Such tests demonstrate the applicability of the antimicrobial agents of this invention. Furthermore, industrial coolant baths were monitored over periods of several months and it has been established that the antimicrobial agent of this invention is effective over considerable periods of weeks without diminution in activity attributable to the controlled release of copper ion upon demand in the coolant baths.

As mentioned above, the metal complexes can be employed in aqueous solution or in solid form. Antimicrobial activities can be achieved upon the addition of an effective amount of either form. Furthermore, it is not necessary to remove other by-product salts from the prepared complexes to achieve the activity. However, by-product water and salt as described in the above procedures may surprisingly be removed to form solid complexes of concentrates. This achieves several goals, e.g., removes a contaminant material which may be detrimental in the utilization of the complex in practical applications, giving rise to excessive salt concentrations or corrosion problems; and enables the preparation of more highly concentrated active ingredient solutions which would enable storage bulk reduction, a definite advantage in industrial applications thereby reducing shipping and storage costs. Also, for other antiseptic, sanitizer, germicidal, bactericidal, sporicidal, virucidal, or disinfectant uses, it may be desirable to have as pure a complex preparation as possible.

Other modifications of this invention and embodiments will become apparent in view of this description, operating examples and presently most preferred forms without departing from its spirit and scope.

What is claimed is:

1. A method of controlling microbes in a medium cnducive to microbial growth which comprises contacting said microbes or said medium with an effective antimicrobial amount of a metal complex of a heavy metal ion and a polyfunctional organic ligand in a ratio of 1:1 of the metal ion to the ligand, said ligand selected from the group consisting of an organic acid and a substituted organic acid, said complex having an aqueous proton induced dissociation property represented by a sigmodially-shaped curve on a cartesian coordinate plot of the negative log of the metal ion concentration versus the negative log of the hydrogen ion concentration, said dissociation property causing the controlled release of metal ions at a pH compatible with the viability of microbes in said medium.

2. The method of claim 1 wherein said metal ion is selected from the group consisting of zinc, nickel, chromium, bismuth, mercury, silver, copper, and cobalt.

3. The method of claim 1 wherein said substituted organic acid is selected from the group consisting of hydroxy polycarboxylic, amino polycarboxylic, sulfhydro polycarboxylic, and phosphinol polycarboxylic.

4. The method of claim 1 wherein said medium has a pH on the order of about 3 to about 12.

5. The method of claim 4 wherein said pH is within the range of about 4 to about 9.

6. The method of claim 1 wherein said pH is alkaline.

7. The method of claim 6 wherein said pH is alkaline within the range of about 9 to about 12.

8. The method of claim 7 wherein said complex is a dialkalimetal monoheavymetal chelate of an alpha-hydroxy polycarboxylic acid.

9. The method of claim 8 wherein said chelate is a dialkalimetal monocopper(II) citrate.

10. The method of claim 9 wherein said chelate is in aqueous admixture.

11. The method of claim 9 wherein said chelate is a solid.

12. The method of claim 1 wherein the metal complex is a dialkalimetal monocopper (II) citrate complex.

13. The method of claim 12 wherein the medium has an alkaline pH.

14. The method of claim 12 wherein the pH range of the medium is from about 7 to about 9 and about 10% to about 0.1% of said copper ion in said complex is released within said range.

* * * * *

UNITED STATES PATENT AND TRADEMARK OFFICE
CERTIFICATE OF CORRECTION

PATENT NO. : 4,055,655
DATED : October 25, 1977
INVENTOR(S) : Gerald L. Maurer et al It is certified that error appears in the above-identified patent and that said Letters Patent are hereby corrected as shown below:

Page 1 at [75] "Shringapurey" should be --Shringarpurey--

Col. 1, line 9 "bacterial" should be --bactericidal--

Col. 3, line 45 "diethylenetriamine-pentaacetic" should be --diethylenetriaminepentaacetic--

Col. 4, line 2 "monomental" should be --monometal--

Col. 4, line 9 "dillthium" should be --dilithium--

Col. 5, line 67 "Introduction" should be --introduction--

Col. 6, line 38 "antimicrobialagents" should be --antimicrobial agents--

Col. 7, line 31 "abour" should be --about--

Col. 7, line 42 "separtory" should be --separatory--

Col. 7, line 43 "breaker" should be --beaker--

Col. 7, line 60 "cyrstals" should be --crystals--

Col. 8, line 11 "aliguots" should be --aliquots--

Col. 8, line 32 "ionspecific" should be --ion specific--

Col. 8, line 34 "coppeer" should be --copper--

UNITED STATES PATENT AND TRADEMARK OFFICE
CERTIFICATE OF CORRECTION

PATENT NO. : 4,055,655
DATED : October 25, 1977
INVENTOR(S) : Gerald L. Maurer et al It is certified that error appears in the above-identified patent and that said Letters Patent are hereby corrected as shown below:

Col. 8, line 64 after "$Cu^{++}$" insert --is available for controlled release; from about 10% to about 0.1% dissociation of $Cu^{++}$--

Col. 9, line 20 "estb" should be --estab--

Col. 9, line 40 "Vosburgan and Vosburgh" should be --Vosburgh and Cooper--

Col. 9, line 52 "comarison" should be --comparison--

Col. 9, line 58 "solution basic solution" should be --strongly basic solution--

Col. 9, line 65 "$2Cu^{++} + \equiv$ Citrate $\underset{}{\overset{\Delta}{\rightleftharpoons}} Cu_2$citrate $\downarrow + H^+$" should be --$2Cu^{++} +$ Citrate $\equiv\underset{}{\overset{\Delta}{\rightleftharpoons}} Cu_2$citrate $\downarrow + H^+$"

Col. 10, line 1 "ration" should be --ratio--

Col. 10, line 4 "it" should be --its--

Col. 11, line 26 "ATCC No." should be in quotation marks

Col. 13, line 1 "__Klebsiella-aerobacter__" to read --__Klebsiella-aerobacter__--

Col. 13, line 4 "micrabilis" should be --mirabilis--

UNITED STATES PATENT AND TRADEMARK OFFICE
CERTIFICATE OF CORRECTION

PATENT NO. : 4,055,655
DATED : October 25, 1977
INVENTOR(S) : Gerald L. Maurer et al It is certified that error appears in the above-identified patent and that said Letters Patent are hereby corrected as shown below:

Col. 14, line 9 "cnducive" should be --conducive--

Signed and Sealed this

Ninth Day of May 1978

[SEAL]

Attest:

RUTH C. MASON
Attesting Officer

LUTRELLE F. PARKER
Acting Commissioner of Patents and Trademarks